United States Patent [19]
Mitsch et al.

[11] 3,972,856

[45] *Aug. 3, 1976

[54] POLYURETHANES CONTAINING POLY(PERFLUOROALKYLENE OXIDES) UNITS

[75] Inventors: Ronald A. Mitsch, Village of Little Canada; Joseph La Mar Zollinger, Village of Maplewood, both of Minn.

[73] Assignee: Minnesota Mining and Manufacturing Company, St. Paul, Minn.

[*] Notice: The portion of the term of this patent subsequent to May 14, 1991, has been disclaimed.

[22] Filed: Oct. 3, 1973

[21] Appl. No.: 403,199

Related U.S. Application Data

[63] Continuation-in-part of Ser. Nos. 805,885, March 10, 1969, abandoned, and Ser. No. 70,540, Sept. 8, 1970, Pat. No. 3,810,874.

[52] U.S. Cl. ............................. 260/77.5 AP; 44/4; 44/7 D; 260/77.5 AM; 260/77.5 AQ

[51] Int. Cl.² .................. C08G 18/30; C08G 18/48
[58] Field of Search ............ 260/77.5 AP, 77.5 AM, 260/77.5 AQ, 77.5 AA

[56] References Cited
UNITED STATES PATENTS
3,810,874    5/1974    Mitsch et al. .................... 260/75 H

*Primary Examiner*—Lester L. Lee
*Attorney, Agent, or Firm*—Alexander, Sell, Steldt & DeLaHunt

[57] ABSTRACT

Low temperature flexible fluorine-containing, elastomeric polyurethane containing poly(perfluoroalkylene oxide) units, $-CF_2O-(CF_2CF_2O)_m(CF_2O)_n-CF_2-$, are prepared, for example, by reacting hydroxy-terminated poly(perfluoroalkylene oxide) with polyisocyanate, said polyurethane being useful in the shape of a seal or gasket or useful as a structural adhesive or a solid propellant binder.

21 Claims, No Drawings

POLYURETHANES CONTAINING POLY(PERFLUOROALKYLENE OXIDES) UNITS

RELATED APPLICATIONS

This application is a continuation-in-part of our copending applications Ser. No. 805,885, filed Mar. 10, 1969, now abandoned, and Ser. No. 70,540, filed Sept. 8, 1970, the latter (now U.S. Pat. No. 3,810,874) being a continuation-in-part of the former. The entire disclosures in said copending applications are relied on and incorporated herein by reference.

This invention relates to functional poly(perfluoroalkylene oxides) and their preparation. In another aspect, it relates to fluorine-containing polyurethanes, and their preparation. In another aspect, it relates to a solid propellant comprising said polyurethanes as a binder therefor. In another aspect, it relates to an admixture of a hydroxy-terminated poly(perfluoroalkylene oxide) and polyisocyanate, said admixture being useful as a structural adhesive or solid propellant binder.

BACKGROUND OF THE PRIOR ART

Polyurethanes have been prepared in the past by reacting hydroxyl-containing hydrocarbon polymers, such as poly(oxypropylene) triols, with aliphatic or aromatic diisocyanates. Such prior art polyurethanes, though widely useful for many applications, do not have the low temperature flexibility, tensile and elongation, and the hydrolytic, thermal, and oxidative stability required for many other applications (such as solid propellant binders and other uses in the aerospace industry). Recently, fluorine-containing polyurethanes have been disclosed in the art which do have some thermal and oxidative stability, but they and their methods of preparation suffer from a number of disadvantages or limitations, as discussed below.

In *Vysokomolekulyarnye Soedineiya* Vol. (A) 9, No. 11, p. 2482 (1967) and *Jour. of Polymer Sci.* Part A-1, Vol. 5, p. 2757 (1967), non-rubbery fluorine-containing polyurethanes are disclosed as being prepared by either the reaction of chloroformate derivatives of hydroxy compounds with fluorine-containing diamines (which reaction evolves corrosive, bubble-forming hydrogen chloride) or the reaction of fluorine-containing hydroxy compounds (rather than prepolymers) with aliphatic diisocyanates. These polyurethanes have a high ratio of urethane groups to the total weight of the polymer, and consequently a low fluorine content. NASA Publication No. SP-5901(01), p. 14 (1968), published by NASA's Office of Technology Utilization, discloses fluorine-containing polyurethanes, having pendant —$CF_3$ groups in the backbone, prepared by reaction of an excess of aliphatic diisocyanate with hydroxyl- and fluorine-containing prepolymers having hydroxyl functionalities typically less than two, using undesirably high reaction temperatures. Though these prior art fluorine-containing polyurethanes do have some thermal and oxidative stability, they do not have very low temperature flexibility — a property which is highly desirable where such products are used, for example, as low temperature adhesives and propellant binders.

BRIEF DESCRIPTION OF INVENTION

Briefly, the polyurethanes of this invention comprise urethane linkages and perfluoroalkylene ether backbone units of the formua —$CF_2O$—$(CF_2CF_2O)_m$($CF_2O)_n$—$CF_2$— where $m$ and $n$ designate randomly distributed perfluoroethyleneoxy and perfluoromethyleneoxy backbone subunits, respectively, the ratio $m/n$ being 0.2/1 to 5/1, preferably 0.5/1 to 2/1 or 0.5/1 to 3/1. These polyurethanes are rubbery polymers of high molecular weight with glass transition temperatures less than −78°C. (and consequently flexible at extremely low temperature) and can be crosslinked. Typically, the polyurethanes have a molecular weight of at least 1100, preferably at least 5000, and frequently as high as 2,000,000 or more. They also have excellent tensile strength and elongation and highly useful degrees of thermal, oxidative, and hydrolytic stability. The low temperature flexibility of the polyurethanes is exceptional, the polyurethanes being flexible at the temperature of dry ice (ca −80°C.) and lower. Such exceptional flexibility can be expressed in terms of glass transition temperature (Tg): the polyurethanes of this invention have a Tg of less than −78°C., and some species have a Tg as low as −125°C. By comparison, commerical fluoro elastomers, such as vinylidene fluoride/perfluoropropylene copolymers, have Tg values only as low as −30°C. Polytetrafluoroethylene has a Tg of +117°C., and oxygen-containing fluorinated polymers such as polytetrafluoroethylene oxide, —$(CF_2CF_2O)_n$—, is a solid at room temperature with a melting point of +37°C. (see U.S. Pat. No. 3,355,397). The lowest Tg of any known fluoro elastomer, viz., a perfluoroalkylene oxide of the formula —$(CF_2CF_2OCF_2CF_2)_n$—, is −65°C. [see *Polymer Letters*, Vol. 6, pp. 335–340 (1968)].

The fluorine-containing polyurethanes of this invention can be prepared by reacting polyisocyanates with linear, hydroxy-terminated, poly(perfluoroalkylene oxide) prepolymers, preferably methylol-terminated prepolymers, having glass transition temperatures (Tg) lower than −78°C. The polyisocyanates preferred in preparing these polyurethanes are the conventional aliphatic or aromatic polyisocyanates, or fluorine-containing aliphatic diisocyanates.

The linear hydroxy-terminated poly(perfluoroalkylene oxides), useful as prepolymers in the preparation of the above-described polyurethanes of this invention, also have exceptionally low glass transition temperatures of less than −78°C. They can be prepared, for example, by reduction of their ester-, carboxy-, or acyl halide-terminated precursors, or prepared by reaction of said ester- or acyl halide-terminated precursors with amino alcohols, said precursors and their preparation being described in Italian Pat. No. 817,809. Hydroxy terminated poly(perfluoroalkylene oxides) having more than two terminal hydroxy groups can be prepared, for example, by reacting the dimethylol-terminated compound with up to two molar equivalents of 2,3-epoxy-1-propanol in the presence of a basic catalyst. Such polyhydroxy derivatives are useful as compatible cross-linking components in the preparation of urethane polymers.

The hydroxy-terminated prepolymer and polyisocyanate reactants can be admixed to form a pourable homogeneous solution which can be cast in a mold and heated to effect crosslinking and solidification at relatively low temperature, e.g. 60°–80°C., or even room temperature if a catalyst is used, without the evolution of volatile byproducts, to form a shaped article, such as an O-ring, gasket, etc., having excellent low temperature flexibility and other desirable properties. Solid rocket propellants of the composite type can be prepared in a conventional manner, using the said solution of prepolymer and polyisocyanate to form a high density thermoset binder for the propellant; however, it is unnecessary to use a plasticizer in order to obtain a workable propellant mixture or a cured propellant with low temperature flexibility when the prepolymer of this invention is used in the binder.

Alternatively, the polyurethanes of this invention can be prepared by reaction of a diol or polyol with an isocyanate-terminated poly(perfluoroalkylene oxide) containing said $-CF_2-(CF_2CF_2O)_m(CF_2O)_n-CF_2-$ units.

DETAILED DESCRIPTION OF THE INVENTION

The linear hydroxy-terminated poly(perfluoroalkylene oxide) reactants or prepolymers used in this invention are preferably those of the general formula:

$$R-CF_2O-(CF_2CF_2O)_m(CF_2O)_n-CF_2-R' \qquad I$$

where R and R' are hydroxy-substituted organic radicals, such as hydroxy-substituted aliphatic or hydroxy-substituted aromatic radicals, or R and R' are preferably methylol, $-CH_2OH$, or $-C(O)N(R'')CH_2C-H_2OH$ (where R'' is hydrogen, lower alkyl, e.g. methyl, or ethylol, $-CH_2CH_2OH$), and m and n designate randomly distributed perfluoroethyleneoxy and perfluoromethyleneoxy backbone units, the ratio m/n being 0.2/1 to 5/1, preferably 0.5/1 to 3/1 and typically 0.7/1 to 1.6/1. The number average molecular weight, $M_n$, is in the range of 500 to 10,000 or 20,000 or higher, preferably 800 to 5000 or 15,000. The glass transition temperature, Tg, of these prepolymers, as well as the polyurethanes prepared therefrom, are much lower than any known fluorine-containing polymers, and in general are lower than −78°C. and preferably lower than −90°C., and can be as low as −125°C., the higher the oxygen-to-fluorine content in the prepolymer, the lower the glass transition temperature. (The "glass transition temperature" of a polymer is that temperature above which a polymer is soft or rubbery, that is, flexible, and below which it is a hard and brittle glass; such temperature is generally determined by differential thermal analysis, "DTA", or changes in coefficient of expansion.) The prepolymers are generally clear, colorless liquids at room temperature, with low bulk viscosity (e.g., 125 cps at 27°C.) properties which are advantageous in using these materials.

Generally, the hydroxy-terminated prepolymer will be a mixture of such compounds having different backbone or chain lengths. Representative prepolymers useful in this invention to form polyurethanes, and coming within the scope of general Formula I above, are the following:

$$HOCH_2-CF_2O-(CF_2CF_2O)_m(CF_2O)_n-CF_2-CH_2OH, \qquad II$$

$$HOCH_2CH_2N(H)C(O)-CF_2O-(CF_2CF_2O)_m(CF_2O)_n-CF_2-C(O)N(H)CH_2CH_2OH, \qquad III$$

$$HOCH_2CH_2N(CH_3)C(O)-CF_2O-(CF_2CF_2O)_m(CF_2O)_n-CF_2-C(O)N(CH_3)CH_2CH_2OH, \qquad IV$$

$$(HOCH_2CH_2)_2NC(O)-CF_2O-(CF_2CF_2O)_m(CF_2O)_n-CF_2C(O)N(CH_2CH_2OH)_2, \qquad V$$

$$HOCH_2-CF_2O-(CF_2CF_2O)_m(CF_2O)_n-CF_2CH_2OCH_2CH(OH)CH_2OH \qquad VI$$

$$HOCH_2CH(OH)CH_2OCH_2-CF_2O-(CF_2CF_2O)_m(CF_2O)_n-CH_2OCH_2CH(OH)CH_2OH, \qquad VII$$

and mixtures thereof.

The simplest methylol-terminated poly(perfluoroalkylene oxide) prepolymers, illustrated by Formula II above, are the preferred prepolymers to be used in this invention because of the greater low temperature flexibility and hydrolytic stability of the polyurethanes prepared therefrom.

The novel methylol-terminated poly(perfluoroalkylene oxides) of this invention can be prepared by reduction of their ester-terminated precursors, such as the lower alkyl esters, e.g.

$$CH_3OOC-CF_2O(CF_2CF_2O)_m(CF_2O)_nCF_2-COOCH_3 \qquad VIII$$

where m and n, and the ratio m/n, are as defined above for Formula I. Such esters can be reduced to the methylol prepolymers by various reduction precedures, such as catalytic hydrogenation in the presence of a copper chromium oxide catalyst (see U.S. Pat. Nos. 2,911,444 and 3,314,987), but preferably they are reduced in the presence of a complex metal borohydride, such as sodium borohydride, $NaBH_4$, the reduction being carried out in an inert solvent, such as tetrahydrofuran, diglyme, or dioxane, and at reflux temperatures. Generally the reaction product will be a mixture of methylol-terminated poly(perfluoroalkylene oxides) of different chain length. If desired, such a mixture can be fractionated, e.g. by distillation, chromatography, selective extraction, and other techniques, to obtain individual fractions of more limited molecular weight distribution.

Instead of reducing the ester-terminated precursors, the corresponding carboxy- or acyl halide-terminated precursors can be reduced, preferably with $LiAlH_4$, to form the methylol-terminated prepolymers. The ethylol-substituted amide-terminated prepolymers illustrated by Formulas III, IV and V above, can be readily prepared by reacting said diester precursors VIII, or said acyl halide precursors, with a corresponding ethanol amine, i.e. $HOCH_2CH_2NH_2$, $HOCH_2CH_2NHCH_3$, and $(HOCH_2CH_2)_2NH$, respectively.

The diester precursors VIII, themselves, and the other precursors mentioned above, and their preparation are disclosed in Italian Pat. No. 817,809 (e.g., Example 11 thereof).

Where the prepolymers have terminal hydroxy-substituted aliphatic groups other than methylol (i.e., prepolymers other than those like Formulas II to V), then can be prepared, for example, by reacting said ester- or acyl halide-terminated precursors with higher aliphatic amino alcohols, such as propanol amine or ω-aminoundecyl alcohol. The hydroxy-substituted aromatic-terminated prepolymers can be prepared, for example, by reacting said acyl halide-terminated precursors with aminophenols, such as m-aminophenol, hydroxyalkyl-substituted aromatic amines, such as hydroxyethylaniline, or hydroxyalkyl-substituted aralkyl amines, such as 1-methyl-1-hydroxymethylbenzylamine. Said acyl halide-or ester-terminated precursors can be converted to other hydroxy-substituted aliphatic or aromatic prepolymers with methylene or substituted methylene linkages between the polymer backbone and the hydroxy-substituted terminal groups. For example, by reacting the acyl halide-terminated precursor with potassium iodide to produce an iodide-terminated intermediate, then reacting the latter with ethylene to produce an iodoethylene- or iodopolyethylene-terminated intermediate, and then saponifying the latter. As another example, said acyl halide- or ester-terminated precursors can be reacted with organometallic compounds, such as ethyl magnesium bromide or mixed methyl and isopropyl magnesium bromides, to produce prepolymers with terminal groups that characterize the prepolymers as tert- or sec-alcohols. As another example, the acyl halide- or ester-terminated precursors can be reacted with excess polyols, such as neopentylglycol, to produce 3-hydroxy-2,2-dimethyl propyl ester terminal groups. The methylol-terminated prepolymers of Formula II can be converted to other hydroxy-substituted aliphatic or aromatic terminated prepolymers with ester or ether linkages in the terminal groups. For example, reaction of the methylol-terminated prepolymer with cyclic esters, such as beta-propiolactone to produce hydroxypropionates; or by reaction with ethylene oxide and/or 1,2-propylene oxide to produce oxyalkylene or polyoxyalkylene diols.

In the event such hydroxy-substituted aliphatic- or aromatic-terminated prepolymers are used rather than he methylol-terminated prepolymers (of Formulas II to V), the aliphatic or aromatic portions of such terminal groups should preferably be less than 15 to 20 weight percent of the prepolymer, and usually contain less than about 12 carbon atoms, in order to retain the desired thermal stability, low temperature flexibility, andother properties imparted to the prepolymers by the perfluoroalkylene ether backbone. Said aliphatic and aromatic portions of said terminal groups should not contain any active hydrogen atoms more reactive with the isocyanato groups of the polyisocyanates than the hydroxy substituent; however, said aliphatic and aromatic portions can contain other substituents which are non-reactive with said isocyanato group.

The polyisocyanates which are admixed and reacted with the hudroxy-terminated prepolymers can be conventional aliphatic or aromatic polyisocyanates. Representative of these polyisocyanates which can be used include: benzene-1,3-diisocyanate; benzene-1,4-diisocyanate; hexamethylene diisocyanate; toluene-2,4-diisocyanate; toluene-2,5-diisocyanate; diphenylmethane-4,4'-diisocyanate; diphenyl-4,4'-diisocyanate; 2-chloropropane-1,3-diisocyanate; 6-chloro-2,4,5- trifluorobenzene-1,3-diisocyanate; diphenyl-3,3'-dimethoxy-4,4'-diisocyanate; naphthalene-1,5-diisocyanate; pentamethylene diisocyanate; tetramethylenediisocyanate; octamethylene diisocyanate; dimethylene diisocyanate; propylene-1,2-diisocyanate; benzene-1,2,4-triisocyanate; toluene-2,3-diisocyanate; diphenyl-2,2'-diisocyanate; naphthalene-2,7-diisocyanate; naphthalene-1,8-diisocyanate; toluene-2,4,6-triisocyanate, benzene-1,3,5-triisocyanate; benzene-1,2,3-triisocyanate; cyclohexane-1,3,5-triisocyanate; toluene-2,3,4-triisocyanate; polymethylene polyphenyl isocyanate; and the like.

Another class of polyisocyanate which can be used in this invention are fluorine-containing aliphatic ether or non-ether diisocyanates of the general formulas:

$$OCN-CH_2-(C_xF_{2x}-O-C_yF_{2y}-_zCH_2-NCO \qquad IX$$

$$OCN-CH_2-(C_xF_{2x}-_zCH_2-NCO \qquad X$$

where $x$ and $y$ are integers of 1 to 8, and $z$ are integers of 1 to 12, preferably 1 to 8. These diisocyanates can be named as $\alpha, \omega$-bis (1,1-dihydroisocyanates). Preferred subclasses of these diisocyanates are those of the general formulas:

$$OCN-CH_2(CF_2)_aO(CF_2)_b-CH_2-NCO \qquad XI$$

$$OCN-CH_2(CF_2)_aO(CF_2)_bO(CF_2)_cCH_2-NCO \qquad XII$$

$$OCN-CH_2[(CF_2)_aO(CF_2)_b]_cCH_2-NCO \qquad XIII$$

$$OCN-CH_2(CF_2)_aCH_2NCO \qquad XIV$$

where $a$, $b$, and $c$ are integers each preferably in the range of 1 to 8, the sum of which in each such formula is preferably 16 or less. Representative fluorine-containing diisocyanates of this type which can be used include $CF_2(CH_2NCO)_2$, $(CF_2CH_2NCO)_2$, $CF_2(CF_2CH_2NCO)_2$, $(CF_2CF_2CH_2NCO)_2$, $CF_2(CF_2CF_2CH_2NCO)_2$, $(CF_2CF_2CF_2CH_2NCO)_2$, $CF_2(CF_2CF_2CF_2CH_2NCO)_2$ $(CF_2CF_2CF_2CH_2NCO)_2$, $O(CF_2CH_2NCO)_2$, $O(CF_2CF_2CH_2NCO)_2$, $O(CF_2CF_2CF_2CH_2NCO)_2$, $OCNCH_2(CF_2)_2O(CF_2)_4CH_2NCO$, $OCNCH_2CF_2OCF(CF_3)CH_2NCO$, $(OCNCH_2CF_2OCF_2)_2$, $OCNCH_2(CF_2OCF_2)_4CH_2NCO$, $OCNCH_2$ $(CF_2OCF_2)_8CH_2NCO$, $OCNCH_2(CF_2C-F_2OCF_2CF_2)_4CH_2NCO$, $OCNCH_2CF_2O(CF_2-)_4OCF_2CH_2NCO$, $OCNCH_2CF$ $(CF_3)OCF_2CF(CF_3)O(CF_2)_5OCF(CF_3)CF_2OCF(CF_3)CH_2NCO$, and the like. These fluorine-containing diisocyanates are particularly useful in that they are more soluble in the hydroxy-terminated prepolymers than the aliphatic or aromatic polyisocyanates, allowing a more rapid attainment of homogeneity, and the resultant polyurethanes have higher thermal stability.

The above fluorine-containing aliphatic diisocyanates can be prepared by reacting phosgene with the corresponding fluorine-containing diamine or diamine hydrochloride precursors which have general formulas like those of Formulas IX and X above, except that inplace of isocyanate groups (—NCO) there are amine groups (—NH$_2$), or amine hydrochloride groups (—NH$_2$.NCl). Preparation of the diisocyanate is preferably carried out by dissolving the diamine precursor in a solvent, such as tetrahydrofuran, diglyme, or chlorobenzene. Alternatively, a slurry of the diamine hydrochloride in these solvents can be prepared. In any event, the phosgene is bubbled through the solution or slurry at a suitable temperature, e.g. 0° to 120°C. for a period of time sufficient to get the desired conversion. For this purpose, the course of phosgenation can be followed by running infrared spectral analysis on withdrawn samples of the reaction mixture. When the infrared spectrum shows the conversion of most of the intermediate carbamoyl chloride to diisocyanate, the solvent is stripped, and the residue distilled to obtain the diisocyanate product.

The oxydiamine precursors themselves can be prepared by reduction of the corresponding diamide or dinitrile precursor with a reducing agent, such as lithium aluminum hydride.

Another class of polyisocyanates which can be used in this invention are isocyanate-terminated poly(perfluoroalkylene oxides) containing said —CF- $_2O-(CF_2CF_2O)_m(CF_2O)_n-CF_2-$ units (hereinafter abbreviated $R_{fo}$), such as

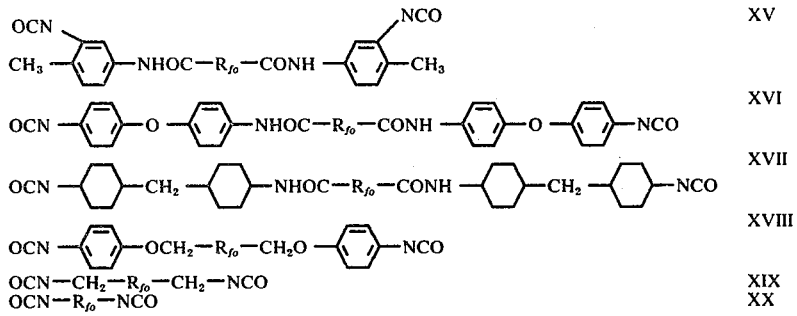

The preparation of these isocyanate-terminated poly(perfluoroalkylene oxides) is described in said copending application Ser. No. 70,540.

The polyurethanes of this invention can be crosslinked materials, possessing a three-dimensional network. The degree of crosslinking can be varied from a low degree of crosslinking, e.g. one crosslink per 500,000 molecular weight units of polymer, to a high degree of crosslinking, e.g. one crosslink per 1000 molecular weight units of polymer. However, a highly crosslinked polyurethane will have a higher glass transition temperature than may be desired, and it may be higher than −78°C.

There are several ways in which the crosslinking of the polyurethanes of this invention can be achieved. The preferred manner of achieving crosslinking of the polyurethanes based on the hydroxy-terminated prepolymer is by reacting difunctional hydroxy-terminated prepolymer with diisocyanate and either triisocyanate or triol, which results both in chain extension of the preplymer and crosslinking by urethane formation. Another manner of achieving crosslinked polyurethanes is by reacting the difunctional hydroxy-terminated prepolymer with a small excess (e.g. 2 to 30%) of diisocyanate, heating to a moderate temperature, e.g. 25° to 80°C., to effect chain extension by urethane formation, and then heating to a higher temperature, e.g. 60° to 150°C., to effect crosslinking by allophanate formation. Another manner of achieving crosslinking is by reacting a mixture of di- and tri-functional hydroxy-terminated prepolymers with diisocyanate. Another manner of crosslinking is to react the difunctional hydroxy-terminated prepolymer with an excess of diisocyanate to produce isocyanato-terminated prepolymer, and reacting the latter with triols (to form urethane linkages) or effecting its trimerization by adding a conventional trimerization catalyst, such as a tertiary amine, e.g. triethylamine or N-methylmorpholine, alkali metal alkoxide, and other strong bases (to effect isocyanurate formation). These various techniques for effecting crosslinking are generally known in the art [e.g. see "Polyurethanes: Chemistry & Technology", Vol. I, by Saunders and Frisch, published by Interscience Publishers, N.Y. (1962)], and further discussion will be omitted in the interest of brevity.

Regardless of the type of polyisocyanate and crosslinking technique used, the amount of polyisocyanate to be used generally will be sufficient to provide a mole ratio of NCO/OH in the range of 0.8/1 to 1.5/1. A stoichiometric amount of the polyisocyanate will be sufficient to form polyurethanes which are rubbery and are useful, e.g. as binders; less than stoichiometric, will give softer polyurethane elastomers having greater elongation under stress, and more than the stoichiometric will generally give harder polyurethanes with higher strengths.

As mentioned above, the polyurethanes of this invention can be rubbery crosslinked polymers, and as such are insoluble in all non-reactive solvents, e.g. alcohols, ketones, esters, hydrocarbons, and halogenated solvents. As an example, they are insoluble in and relatively unaffected by jet fuels, and are particularly useful in this respect as sealants for fuel tanks and as gaskets and O-rings, and in structural adhesives which come into contact with such fuels. Unlike their prepolymers, the polyurethanes are insoluble in fluorinated ether solvents, such as FC-75, but swell therein. The polyurethanes are of relatively high density, which means that when they are used as binders for solid propellants, the density impulse thereof is enhanced. The exceptionally low Tg of these polyurethanes is another property which enhances their use as such binders, as well as their use in cryogenic adhesives and structural metal-to-metal adhesives for airframes where low temperature flexibility is required. Generally, the higher the number average molecular weight, $M_n$, of the hydroxy-terminated prepolymer used in making the polyurethane, the lower the Tg. ($M_n$ as used herein is determined by vapor phase osmometry.) Their hydrolytic stability is excellent and means that they can be used in the form of shaped articles, such as gaskets, seals, etc., which are subject to moisture contact during use or which come into contact with aqueous solvents or water. They also have useful degrees of thermal and oxidative stability, tensile strength and elongation, and do not support combustion in air.

The hydroxy-terminated prepolymer and polyisocyanate, and crosslinking polyol where used, can be admixed to form a homogeneous solution. In order to get this homogeneous solution, it may be necessary to heat the mixture, e.g. 1–2 hours at 60°–100°C., and get a partial reaction between the components. The addition of catalyst, such as N-methylmorpholine, conventionally used in making polyurethanes from polyols, will speed the attainment of homogeneity. Alternatively, cosolvents, such as 1,2-dimethoxyethane, tetrahydrofuran, and fluorinated solvents, can be used to form a solution, the solvent thereafter being stripped. The reaction mixture can be poured or cast in a mold of desired shape, and the material heated to effect curing or crosslinking. Curing temperatures in the range of 25° to 125°C. will be useful in general, depending on the particular polyisocyanate and prepolymer, and whether curing catalysts are used. Higher temperatures, e.g. up to 200°C., are not necessary, and may result in decomposition of the urethane linkages. The use of curing catalyst, such as tertiary amines, e.g., N-methyl morpholine, ferric acetyl acetonate, stannous octoate, and di-n-butyl tin diacetate, etc., in catalytic amounts (generally 0.005 to 1 wt. %, preferably 0.01 to 0.5 wt. %, based on the weight of prepolymer), will enable the use of lower curing temperatures, e.g. 25° to 40°C. In any case, the optimum curing temperature and duration of cure, can be determined empirically by simple routine tests.

In some applications of the polyurethane of this invention, it may be desirable to use a plasticizer to facilitate the mixing or compounding of the prepolymer with other materials, such as fillers, e.g. diatomaceous earth, or propellant ingredients, e.g. oxidizer, fuel, etc. However, the use of plasticizers is not essential, especially where the polyurethanes of this invention are used as binders for solid rocket propellants.

The polyurethane products of this invention can be used as high density binders in solid rocket propellants of the castable composite type. In such application, the general procedure used involves blending the admixture or solution of methylol-terminated prepolymer and polyisocyanate with energetic fuel (e.g. aluminum powder), and/or propellant oxidizer (e.g. ammonium perchlorate), and other conventional propellant additives, shaping the resulting mixture in the form of a grain by means of casting the mixture in a mold, and then heating the shaped grain at elevated temperatures to effect the crosslinking of the prepolymer by the diisocyanate to form a finished grain.

Generally, the propellant oxidizer will be an inorganic oxidizing salt, such as the ammonium, alkali metal, and alkaline earth metal salts of nitric, perchloric, and chloric acids. Mixtures of these oxidizing salts can also be used. Ammonium nitrate and ammonium perchlorate are the preferred oxidizers for use in the solid propellant compositions of this invention. Other applicable oxidizers representatively include sodium nitrate, potassium perchlorate, strontium chlorate, lithium chlorate, calcium nitrate, barium perchlorate, and the like. In the preparation of the propellant compositions, the oxidizers are powdered to sizes generally in the range of from 1 to 300 microns average particle size, preferably in the range between 20 and 200 microns. The propellant fuel will be a powdered or finely divided metal, such as aluminum or boron, e.g. with a particle size in the range of 20 to 200 microns.

The amount of solid oxidizer and fuel (e.g. powdered aluminum) employed will usually be a major proportion of the total composition, and is generally in the range between 50 and 85 percent by weight of the total mixture. The binder in the propellant composition will usually be a minor proportion of the total composition, and is generally in the range between 15 and 50 percent by weight of the total mixture.

The propellant compositions of this invention can also contain various other conventional compounding ingredients, such as antioxidants, wetting agents, curing agents, metal oxides, reinforcing agents, powdered metals, and the like. The finished "propellant" usually contains these other compounding ingredients, and the quoted term will be used generically herein to cover the mixture of the fluorocarbon polymer with these other ingredients, unless otherwise noted.

The propellant composition of this invention can be formed into a grain having any desired shape or geometry, such as grains of the internal, external, and internal-external burning types, and geometries which provide progressive, neutral, or degressive modes of burning.

Further details on the use of polyurethanes of this invention as propellant binders will be omitted in the interest of brevity, since the physical and manipulative steps in preparing solid propellants is well-known in the art (see, for example U.S. Pat. No. 3,050,423).

Objects and advantages of this invention are further illustrated by the following examples, but the particular materials and amounts thereof recited in these examples, as well as other conditions and details, should not be construed to unduly limit this invention.

EXAMPLE 1

This example describes the preparation of a methylol-terminated poly(perfluoroalkylene oxide) reactant used in this invention.

Powdered lithium aluminum hydride (1.9 g., 0.05 mole) was added to 120 ml. of dry diethyl ether in a 500 ml., three-necked flask fitted with a mechanical stirrer, a reflux condenser fitted with a Drierite drying tube, and a gas-inlet tube, and the mixture stirred 4 hrs. under dry nitrogen. Fifty ml. of an ether solution of the methyl diester precursor (see Formula VIII above, where $M_n$ was 1800 and $m/n$ was 1.4/1) was added to the stirred solution of lithium aluminum hydride at a rate sufficient to maintain a gentle reflux. After all the ester had been added, the resulting mixture was heated at reflux overnight. Anhydrous methyl alcohol (20 ml.) was added to decompose the excess hydride, followed by addition of dilute sulfuric acid (37 g. of 36N $H_2SO_4$ in 100 ml. of water). The aqueous and organic layers were separated and the aqueous layer extracted 4 times with diethyl ether, and the resulting ether fractions and the organic layer combined and dried over calcium sulfate. The calcium sulfate and ether were removed from the combined ether fractions, yielding 32.5 g. of water-white, liquid methylol-terminated poly(perfluoroalkylene oxide), $HOCH_2-CF_2O-(CF_2CF_2O)_m(CF_2O)_n-CF_2-CH_2OH$, which was found to have a $M_n$ of about 1800, a hydroxyl equivalent weight of 975 ± 50, and a $T_g$ of −107°C.

EXAMPLE 2

In this example, another methylol-terminated poly(-perfluroalkylene oxide) was prepared following the procedure of Example 1, using a similar methyl diester precursor ($M_n$ of 3000, $m/n$ = 1.25/1) except that Freon 113 trichlorotrifluoroethane was used for extraction instead of diethyl ether. The preparation yielded 40 g. of water-white, liquid methylol-terminated fluoro polymer, $HOCH_2-CF_2O-(CF_2CF_2O)_m(CF_2O)_n-CF_2-CH_2OH$, which was found to have a $M_n$ about 3000, and hydroxyl equivalent weight of 1550 ± 50.

EXAMPLE 3–7

In these examples, a number of polyurethanes of this invention were prepared using the methylol-terminated prepolymers of Example 1 ($M_n$ 1800) or Example 2 ($M_n$ 3000).

In each sample, 5,46 g. of the methylol-terminated prepolymer and 0.08 g. of a 3 wt. % solution of N-methylmorpholine in acetone were mixed in a 10 ml. beaker. To the resulting solution, 0.34 g. of an isocyanate mixture was added, made up of 33 wt. % cyclohexane triisocyanate and 67 wt. % of hexamethylene diisocyanate. After mixing initially at 25°C., the mixture was heated for about 1 hr. at 80°C. and then cast in a mold in the form of a bar and heated at 80°C. overnight, to produce a gelled polyurethane product which became tack-free in 48 hrs. After 4 days at 80°C., the cured polyurethane was removed from the mold and its physical properties determined. (In two of the runs, Example 5 and 7, the bar was further cured for 24 hrs. at 125°C. before removal from the mold.) Results are summarized in Table I below:

TABLE I

| | Example | | | | |
|---|---|---|---|---|---|
| | 3 | 4 | 5 | 6 | 7 |
| Prepolymer, $M_n$ | 3000 | 3000 | 3000 | 1800 | 1800 |
| NCO/OH equiv. ratio | 1.15 | 1.36 | 1.39 | 1.12 | 1.36 |
| Cure in hrs at: 80°C. | 96 | 96 | 24 | 96 | 24 |
| 125°C. | — | — | 24 | — | 24 |
| Hardness, Shore A-2 | 5 | 12 | 15 | 20 | 30 |
| Density, g/cc. | 1.79 | 1.79 | 1.78 | 1.76 | 1.73 |
| $T_g$ by DTA$^a$, °C. | −112 to −104 | −112 to −103 | −113 to −104 | −102 to −92 | −101 to −90 |
| Tensile strength$^b$, psi | 50 | 65 | 80 | 60 | 135 |
| Elongation, % | 440 | 280 | 260 | 150 | 185 |
| TGA$^c$-Temp. at 10% Weight Loss | 375°C. | 324°C. | 322°C. | 304°C. | 312°C. |

$^a$ "DTA" means the $T_g$ was determined by differential thermal analysis.
$^b$ Tensile strengths given are averages of two specimens, determined at break.
$^c$ "TGA" means weight loss was determined by thermogravimetricanalysis.

Small strips of the polyurethanes of Examples 3 and 6 were immersed in a trichloroethylene-dry ice bath and cooled to bath temperature (−78°C.). The cooled strips could be repeatedly bent into U and S shapes without breaking, showing that they were flexible at this temperature and that they had $T_g$ values of less than −78°C. By contrast, a strip of high molecular weight polyurethane ($T_g$ = −55°C.) made from $HOCH_2(CF_2CF_2OCF_2CF_2)_nCH_2OH$ and hexamethylene diisocyanate became hard when cooled in the bath and broke into several pieces when bent.

EXAMPLE 8

A polyurethane was prepared by mixing 2.39 g. of the prepolymer of Example 1 with 0.41 g. of tetrafluorophenylene diisocyanate in a 5 cc. beaker at 25°C. and then further heated for about 2¼ hrs. at 80°C. with frequent mixing. The resulting mixture was cast in a mold to form a bar, the cast sample gelling in 4–5 hrs. at 80°C. and becoming tack-free overnight. The cure of the sample bar was completed by heating at 125°C. for 24 hrs. The resulting cured polyurethane elastomer was found to have a density of 1.88 g/cc Shore A-2 hardness of 50, $T_g$ of −100° to −86°C., a tensile strength of 965 psi, and an elongation of 850%.

EXAMPLE 9

A polyurethane was prepared by mixing 0.74 g. of the prepolymer of Example 1 with 0.015 g. of a 3% solution of dibutyl tin diacetate in acetone, followed by the addition of 0.097 g. of toluene diisocyanate. The mixture was heated at 80°C. with frequent stirring, and the product gelled in about 1 hr. to form a tough polyurethane elastomer.

EXAMPLE 10

A solution was prepared by mixing in a 10 cc. vial 0.05 g. of the prepolymer of Example 1, 0.009 g. of a 3 wt. % solution of N-methylmorpholine in acetone, 0.080 g. of polymethylene polyphenylisocyanate (PAPI), and 1.5 ml. of 1,2-dimethoxyethane solvent. The solution became clear after mixing for 10 min. at 40°C., and mixing was continued overnight at this temperature. The solvent was then removed from the mixture under reduced pressure, producing an opaque tan liquid which gelled in 20 min. at 80°C., and then cured for 4 days at 80°C. resulted in a tough polyurethane elastomer, having a $T_g$ of −104° to −92°C.

EXAMPLE 11

In this example, an ethylol-substituted, amide-terminated prepolymer was prepared by slowly adding and stirring 0.9 g. of ethanol amine to 10.2 g. of a methyl diester precursor like that used in Example 1 with $M_n$ = 1400 and $m/n$ = 1.55/1. After stirring the mixture for 1 hr., infrared analysis indicated complete conversion of the ester precursor to the amide-terminated prepolymer. The reaction mixture was dissolved in 125 ml. diethyl ether, washed with 3–10 ml. portions of water, and dried over calcium sulfate. Removal of the calcium sulfate and ether yielded 9.5 g. of the pale yellow prepolymer having the structure shown by Formula III above.

EXAMPLE 12

Amide-terminated prepolymer (4.2 g.) of Example 11 was mixed with 0.5 g. of hexamethylene diisocyanate, and then heated at 80°c. with frequent mixing, producing a homogeneous mixture in 1 hr., and a tough strong flexible tack-free polyurethane in 48 hrs.

EXAMPLE 13

Amide-terminated prepolymer (4.9 g.) of Example 11 was mixed with 0.78 g. of toluene diisocyanate, then heated for 2 hrs. at 80°C. to produce a homogeneous mixture which gelled in 6½ hrs. and was tack-free in 24 hrs., the resulting polyurethane elastomer being tough, and firm.

EXAMPLE 14

An ethylol-substituted, amide-terminated prepolymer was prepared by mixing 4.2 g. of the same ester precursor used in Example 11 with 0.47 g. of 2-(methyl amino)ethanol. The resulting product was dissolved in 50 ml. diethyl ether, washed with two 15 ml. portions of 5% aqueous hydrochloric acid, followed by washing with three 10 ml. portions of water, and dried over calcium sulfate. Removal of the calcium sulfate and ether yielded 4 g. of pale yellow prepolymer having the structure shown in Formula IV above.

EXAMPLE 15

One-half g. of amide-terminated prepolymer of Example 14 was mixed with 0.078 g. of toluene diisocyanate, and heated at 80°C. with frequent stirring, the mixture becoming homogeneous in 30 min., gelling in less than 24 hrs. and becoming tack-free in 48 hrs., the resulting polyurethane elastomer being flexible and firm.

EXAMPLE 16

This example illustrates the use of the polyurethane of this invention as a structural adhesive.

Amide-terminated prepolymer (0.66 g.) of Example 11 was mixed with 0.098 g. of toluene diisocyanate. After 2 hrs. at 80°C., the homogeneous mixture was spread on a 3.5 × 1.5 inch acid-etched aluminum panel and another aluminum panel pressed thereover to form a ½ inch overlap shear specimen, the assembly then being cured at 80°C. for 2 hrs. The cured specimen was then tested on an Instron machine at 23°C., the bond failing only after application of a shear force of 1200 psi.

EXAMPLE 17

This example illustrates the use of the polyurethane of this invention as a binder for a cast propellant.

Methylol-terminated prepolymer (0.41 g.) of Example 1 was mixed with 0.009 g. of a 3 wt. % solution of N-methylmorpholine in acetone, and 0.059 g. of the isocyanate mixture used in Example 3. The resulting mixture became homogeneous in 35 min. at 80°C., and it was mixed with 0.49 g. of aluminum powder and 0.956 g. of ammonium perchlorate. The resulting propellant mixture was then pressed in a mold and heated for 2 days at 80°C. to form a bar of cured solid propellant which was firm and flexible and burned with a bright flame when ignited.

EXAMPLE 18

A methyl diester precursor (see Formula VIII), $M_n = 1940$, $m/n = 0.7/1$, was fractionated by precipitation and the molecular weight distribution of each fraction determined by vapor phase osmometry. Results are shown below.

TABLE II

| Fraction | $M_n$ | Wt. % |
| --- | --- | --- |
| 1 | 1090 | 12 |
| 2 | 1800 | 17 |
| 3 | 2000 | 7 |
| 4 | 2350 | 10 |
| 5 | 2850 | 15 |
| 6 | 3000 | 14 |
| 7 | 3350 | 8 |
| 8 | 3750 | 8 |
| 9 | 4650 | 6 |
| 10 | 7830 | 2 |
| 11 | >7830 | 1 |

The above diester ($M_n = 1940$) was reduced following the procedure of Example 2 and the resulting methylol-terminated prepolymer was used to prepare a polyurethane following the procedure of Example 3, using 2.61 g. of the prepolymer, 0.028 g. of catalyst solution (3 wt. % N-methylmorpholine in acetone), and 0.254 g. of a mixture of 80 wt. % hexamethylene diisocyanate and 20 wt. % cyclohexane triisocyanate, and mixing these materials at 80°C. The mixture became homogeneous in 30 min., gelled in 3 hrs., and was tack-free in 24 hrs. The product was then further cured 24 hrs. at 80°C. and 24 hrs. at 125°C., and the fully cured product had a Shore A-2 hardness of 15, a tensile strength at break of 70 psi, an elongation at break of 200%, and a density of 1.8 g./cc.

A sample of the above polyurethane elastomer was heated in air at about 150°C. and weight loss determined by repeated weighings. Results are shown in Table III.

TABLE III

| Time, hrs. | Wt. Loss, % |
| --- | --- |
| 24 | 0.8 |
| 72 | 1.2 |
| 165 | 1.4 |
| 260 | 1.9 |
| 430 | 3.2 |

The sample had become amber in color after this heat aging treatment, but was still very flexible, even when cooled to dry ice temperature.

EXAMPLE 19

One gram of a methylol-terminated prepolymer ($M_n = 1700$, $m/n = 0.7$), having the structure shown by Formula II above and prepared by reduction of the corresponding methyl diester using the procedure of Example 1, was mixed with 0.011 g. of catalyst solution (3 wt. % N-methylmorpholine), and 0.150 g. of hexamethylene diisocyanate, the mixing being carried out at 80°C. for about 30 min. until a homogeneous mixture was achieved. Then 0.026 g. of 1,2,6-hexanetriol was mixed in and the mixture heated at 80°C. A gel was obtained in less than 24 hrs. and the product was tack-free in 48 hrs. The resulting polyurethane elastomer was tough, flexible, and had good strength and elongation.

EXAMPLE 20

A 250 ml. flask was charged with 100 ml. of anhydrous ethyl ether and 12.74 g. of the methyl diester precursor used in Example 11. The mixture was cooled with an ice bath to about 5°C. and stirred. To the stirred solution, 0.38 g. of diethanol amine was slowly added, followed by adding 1.21 g. of 2-aminoethanol. The resulting mixture was warmed to room temperature and mixing continued for 2 hrs. The solution was then washed 4 times with 25 ml. portions of water, dried over calcium sulfate, filtered, and the ether solvent stripped off. The resulting mixed amide-terminated prepolymer amounted to 12.8 g. and was a pale yellow liquid. Using the procedure of Example 13, 0.634 g. of the mixed amide-terminated prepolymer was reacted with 0.090 g. of hexamethylene diisocyanate at 80°C. The resulting mixture became homogeneous in about 30 min., gelled in 24 hrs., and was tack-free after 2 days. The resulting polyurethane elastomer was tough and flexible.

EXAMPLE 21

In a small beaker, 5.59 g. of the methylol-terminated prepolymer of Example 1 was mixed with 0.08 g. of catalyst solution (3 wt. % N-methylmorpholine in acetone), and 1.13 g. of a fluorinated aliphatic diisocyanate, $O(CF_2CF_2CH_2NCO)_2$, the mixture being warmed to 80°C. with intermittent mixing. The mixture became homogeneous in 10 min., gelled in less than 24 hrs., and was tack-free in 48 hrs. The resulting polyurethane elastomer was firm and flexible.

(The fluorinated diisocyanate used above was prepared by esterifying $O(CF_2CF_2COOH)_2$ with methanol, ammonolysis of the resulting diester, and reduction of the resulting diamide with $LiAlH_4$ to produce $O(CF_2CF_2CH_2NH_2)$, b.p. 94°C./23 mm, $n_D^{22}$ 1.3507. The diamine was phosgenated, refluxed in glyme for 2 days, and the reaction mixture distilled to produce the diisocyanate, $O(CF_2CF_2CH_2NCO)_2$, b.p. 62°C./0.4 mm, $n_D^{22.5}$ 1.3668).

EXAMPLE 22

Twenty grams of the same methylol-terminated prepolymer used in Example 19 was dissolved in 20 ml. of Freon 113 trichlorofluoroethane, and the resulting solution poured into 200 ml. of methanol while stirring vigorously. The prepolymer fraction which settled out was removed and stripped at reduced pressure, yielding 13 g. of prepolymer fraction, $M_n = 2840$. Using the procedure of Example 3, 8.52 of the prepolymer fraction was mixed at 80°C. with 0.14 g. of catalyst solution (3 wt. % N-methylmorpholine in acetone), and 0.47 g. of hexamethylene diisocyanate mixed with 20 wt. % cyclohexanetriisocyanate. The mixture became homogeneous in 2 hrs. and gelled in 48 hrs. at 80°C. After curing for 5 days at 80°C., the resulting soft polyurethane elastomer was slightly tacky, had a tensile strength at break of 48 psi., an elongation at break of 860%, a Shore A-2 hardness of 2, zero % permanent set after 10 min., and the product appeared to retain these properties after heating in air overnight at 150°C.

EXAMPLE 23

Small strips of polyurethanes of Examples 3, 4, 6 and 8 were soaked for 7 days in a refluxing jet fuel reference fluid (consisting of 30 parts toluene, 60 parts cyclohexane, and 10 parts isooctane, these being parts by volume), the refluxing temperature being 85°C. The samples so treated exhibited only 2–4% linear swell and 2–4% weight gain, with no apparent changes in physical properties. After standing for 7 days in air at room temperature, the samples lost only 2–4% of initial weight (i.e. weight before soaking).

EXAMPLE 24

Small strips of the polyurethanes of Examples 4, 7, and 8 were soaked for 10 days at 25°C. in FC-75 fluorocarbon ether solvent, and the physical properties of the so-treated samples determined as shown in Table IV.

TABLE IV

| Polyurethane of | Vol. % swell* | % wt. gain* | % wt. loss** |
|---|---|---|---|
| Example 4 | 35 | 150 | 4.8 |
| Example 7 | 18 | 65 | 1.5 |
| Example 8 | 22 | 60 | 1.0 |

*These values were determined while treated samples were still wet with FC-75.
**These values were determined after the samples stood for 7 days in air at room temp.

EXAMPLE 25

A sample strip of the polyurethane of Example 7 was suspended over vigorously boiling water, so as to completely envelop the sample in steam (ca 100°C.). The sample was periodically removed from the steam, dried at 60°C., and its weight loss determined, and the steam treatment continued. After 45 days, the sample lost only 7.5% of its initial weight and slightly decreased in strength and slightly increased in elongation.

EXAMPLE 26

Amides free of isocyanate-reactive hydrogen atoms, such as the compounds of Formulas XV, XVI and XVII, can conveniently be prepared from carboxy-terminated poly(perfluoroalkylene oxides):

$$HO_2CCF_2O-(CF_2CF_2O)_m(CF_2O)_n-CF_2CO_2H \qquad XXI$$

in accordance with this example.

To a refluxing solution of 90 g. of toluene 2,4-diisocyanate in 150 ml. of xylene hexafluoride in a 500 ml. glass flask was added, over a two hour period, 50 g. of a dicarboxylic acid of formula XXI ($Mn = 2700$, $m/n = 0.6$) in 25 ml, of xylene hexafluoride. Refluxing was continued for 2 days to complete the reaction and to eliminate carbon dioxide. Most of the solvent was removed by distillation and the cooled reaction mixture washed four times with petroleum ether. The pure isocyanate-amide end-capped liquid polymer (42 g.) was isolated by pumping under good vacuum at room temperature.

Infrared absorptions at 3.05 and 6.5 microns for NH, 4.40 microns for NCO, and 5.87 microns for C=O, are consistent with the structure:

$$OCNC_6H_3(CH_3)NHC(O)CF_2O-(CF_2CF_2O)_m(C-F_2O)_nCF_2CONHC_6H_3(CH_3)NCO$$

EXAMPLE 27

Another type of hydroxy-terminated poly(perfluoroalkylene oxide), containing more than one hydroxyl group on each terminating radical, was prepared as shown in this example.

To a 500 ml round bottom glass flask was charged 105 g. of a methylol-terminated poly(perfluoroalkylene oxide) diol ($M_n=2000$, $m/n=0.6$) like that prepared in Example 1. The system was degassed and blanketed with $N_2$, then 5.25 ml. of a $NaOCH_3$ solution in methanol (4.85 meq./g) was added through a syringe with magnetic stirring. Methanol was removed under reduced pressure while the mixture was heated to 65°C. The system was again blanketed with $N_2$, cooled to 45°C., and 1.85 g. of glycidol was added. After the mixture was stirred at 90°C. for 1½ hours it was cooled, diluted with 150 ml. $CF_2ClCFCl_2$ and washed with 10 ml of 10% aqueous $H_2SO_4$. The solution was dried, filtered and concentrated. After a final heating to 95°C. at 0.8 mm Hg the product was filtered through a sintered glass funnel to remove trace contaminants. 98.5 grams (92.5%) of a yellow clear product was obtained, a 50% solution of the polycarbinol $$HOCH_2CF_2O(CF_2CF_2O)_m(CF_2O)_n CF_2CH_2OCH_2CH(OH)CH_2OH$$

in unreacted diol. By using a 2:1 mol ratio of glycidol to diol instead of the 0.5:1 illustrated above, a completely di-substituted product was obtained. The product is useful as a crosslinking agent for urethane or polyester polymers.

EXAMPLE 28

This example illustrates the preparation of a polyurethane from a mixture of a hydroxy-terminated poly(- perfluoroalkylene oxide) and an isocyanate-terminated poly(perfluoroalkylene oxide).

A polyurethane was prepared by mixing 0.6 of $OCNCH_2CF_2(OCF_2CF_2)_m(OCF_2)_nOCF_2CH_2NCO$, $Mn = 740$, $m/n = 0.8$, with 0.75 g. of the dicarbinol prepared in Example 1 and 0.757 g. of the polycarbinol solution prepared in Example 27 above to achieve an NCO/OH ratio of about 1.01. The homogeneous mixture was cast into a mold and heated at 80° to 120°C. until the sample was tack-free. The resulting cured polyurethane elastomer was flexible at −78°C. and showed no loss of strength when heated for 6 days at 300°F.

EXAMPLE 29

This example illustrates the preparation of a polyurethane from a hydroxy-terminated poly(perfluoroalkylene oxide).

Two moles of the methylol-terminated prepolymer prepared in Example 1 was reacted with 1 mole of glycidol in the presence of sodium methoxide. The reaction mixture was heated to 90°C. and held at that temperature for 1.5 hrs., after which the mixture was allowed to stand and cool overnight. The reaction mixture was dissolved in trichlorotrifluoroethane (Freon-113). The solution was washed with 10% aqueous sulfuric acid and then washed with saturated aqueous sodium chloride and dried over magnesium sulfate. The dried solution was filtered and concentrated under reduced pressure to yield a yellow liquid hydroxy-terminated prepolymer; it had an equivalent weight of 830 and hydroxyl functionality of 2.4.

One gram of the above-prepared prepolymer product, 1.0 g. of said methylol-terminated prepolymer of Example 1, 0.010 g. of a 3% solution of dibutyl tin diacetate in acetone, and 0.175 g. of oxy-bis(ethylosocyanate), $O(CH_2CH_2NCO)_2$, were mixed and heated at 60°C. After 20 min. of intermittent stirring, the mixture was homogeneous and clear. It gelled in 1 hr., became tack-free in 4 hrs. and cured in 48 hrs. at 60°C. The resulting polyurethane rubber was flexible and did not break when bent repeatedly at −78°C.

Various modifications and alterations of this invention will become apparent to those skilled in the art without departing from the scope and spirit of this invention, and it should be understood that this invention is not to be unduly limited to the illustrative embodiment set forth herein.

What is claimed is:

1. Polyurethane having a glass transition temperature lower than −78°C. and comprising urethane linkages and backbone units of the formula $$-CF_2O-(CF_2CF_2O)_m(CF_2O)_n-CF_2-$$

where $m$ and $n$ designate randomly distributed perfluoroethyleneoxy and perfluoromethyleneoxy backbone subunits, respectively, the ratio $m/n$ being 0.2/1 to 5/1.

2. Polyurethane according to claim 1, wherein said ratio $m/n$ is 0.7/1 to 1.6/1, and said glass transition temperature is lower than −90°C.

3. Polyurethane according to claim 1, wherein said backbone units have a number average molecular weight of 500 to 20,000.

4. Polyurethane according to claim 1, wherein said backbone units have a number average molecular weight of 500 to 10,000.

5. Polyurethane according to claim 1, wherein said backbone units have a number average molecular weight of 800 to 5000.

6. Polyurethane according to claim 1, wherein said ratio $m/n$ is 0.7/1, said backbone units have a number average molecular weight of 1700 to 2840, and said glass transition temperature is less than −100°C.

7. In a method of preparing polyurethane by reacting polyisocyanate reactant with diol or polyol reactant, the improvement comprising using as either or both of said reactants a material having backbone units of the formula:

$$-CF_2O-(CF_2CF_2O)_m(CF_2O)_n-CF_2-$$

where $m$ and $n$ designate randomly distributed perfluoroethyleneoxy and perfluoromethyleneoxy backbone subunits, respectively, the ratio $m/n$ being 0.2/1 to 5/1.

8. The method according to claim 7 wherein said diol or polyol reactant is linear hydroxy-terminated poly(perfluoroalkylene oxide) having the general formula:

$$R-CF_2O-(CF_2CF_2O)_m(CF_2O)_n-CF_2-R'$$

where R and R′ are hydroxy-substituted organic radicals, and $m$ and $n$ designate randomly distributed perfluoroethyleneoxy and perfluoromethyleneoxy backbone subunits, respectively, the ratio $m/n$ being 0.2/1 to 5/1.

9. The method of claim 8, wherein R and R′ are methylol or $-C(O)N(R'')CH_2CH_2OH$, and R″ is hydrogen, lower alkyl of 1 to 8 carbon atoms, or ethylol.

10. The method of claim 8, where R and R′ are methylol.

11. The method of claim 8, where R and R′ are $-C(O)N(H)CH_2CH_2OH$.

12. The method of claim 8, where R and R′ are $-C(O)N(CH_3)CH_2CH_2OH$.

13. The method of claim 8, where R and R′ are $-C(O)N(CH_2CH_2OH)_2$.

14. The method of claim 8, wherein said ratio $m/n$ is 0.7/1 to 1.6/1, and said glass transition temperature is lower than −90°C.

15. The method of claim 8, wherein said poly(perfluoroalkylene oxide) had a number average molecular weight of 500 to 20,000.

16. The method of claim 8, wherein said poly(perfluoroalkylene oxide) had a number average molecular weight of 500 to 10,000.

17. The method of claim 8, wherein said poly(perfluoroalkylene oxide) has a number average molecular weight of 800 to 5000.

18. The method of claim 8, where R and R′ are methylol, said ratio $m/n$ is 0.7/1, said glass transition temperature is less than −100°C., and poly(perfluoroalkylene oxide) has a number average molecular weight of 1700 to 2840.

19. The method according to claim 7 wherein said polyisocyanate reactant is isocyanate-terminated poly(perfluoroalkylene oxide) having backbone units of the formula $$-CF_2O-(CF_2CF_2O)_m(CF_2O)_n-CF_2-$$

where $m$ and $n$ designate randomly distributed perfluoroethyleneoxy and perfluoromethyleneoxy backbone subunits, respectively, the ratio $m/n$ being 0.2/1 to 5/1.

20. The method according to claim 19, wherein said isocyanate-terminated poly(perfluoroalkylene oxide) is $$OCNCH_2-CF_2-(CF_2CF_2O)_m(CF_2O)_n-CF_2-CH_2-NCO.$$

21. A shaped article comprising the polyurethane of claim 1.

* * * * *

UNITED STATES PATENT AND TRADEMARK OFFICE
CERTIFICATE OF CORRECTION

PATENT NO. : 3,972,856
DATED : August 3, 1976
INVENTOR(S) : Ronald A. Mitsch

It is certified that error appears in the above-identified patent and that said Letters Patent are hereby corrected as shown below:

Col. 5, line 28, "he" should read -- the --;

Col. 5, line 35, "andother" should read -- and other --;

Col. 5, line 43, "hudroxy-terminated" should read -- hydroxy-terminated --;

Col. 5, line 66, the formula should read
-- $OCN-CH_2-(C_xF_{2x})-O-(C_yF_{2y})_z-CH_2-NCO$ --;

Col. 6, line 1, the formula should read
-- $OCN-CH_2-(C_xF_{2x})_z-CH_2-NCO$ --;

Col. 6, line 45, "inplace" should read -- in place --;

Col. 7, line 38, "preplymer" should read -- prepolymer --;

Col. 11, line 27, "thermogravimeticanalysis" should read -- thermogravimetric analysis --;

Col. 13, line 43, "molecular 25 weight" should read -- molecular weight --.

Signed and Sealed this

Sixth Day of September 1977

[SEAL]

Attest:

RUTH C. MASON
Attesting Officer

LUTRELLE F. PARKER
Acting Commissioner of Patents and Trademarks